(12) United States Patent
Zhong et al.

(10) Patent No.: US 10,132,250 B2
(45) Date of Patent: Nov. 20, 2018

(54) EXHAUST PARAMETER BASED DUAL FUEL ENGINE POWER VIRTUAL SENSOR

(71) Applicant: Cummins Inc., Columbus, IN (US)

(72) Inventors: Jinghua Zhong, Bloomington, IN (US); C. Larry Bruner, Greenwood, IN (US); John F. Wright, Columbus, IN (US); Timothy P. Lutz, Columbus, IN (US); Phanindra Garimella, Bloomington, IN (US); Jacob A. Brown, Columbus, IN (US)

(73) Assignee: Cummins Inc., Columbus, IN (US)

(*) Notice: Subject to any disclaimer, the term of this patent is extended or adjusted under 35 U.S.C. 154(b) by 360 days.

(21) Appl. No.: 14/732,979

(22) Filed: Jun. 8, 2015

(65) Prior Publication Data

US 2015/0354472 A1  Dec. 10, 2015

(30) Foreign Application Priority Data

Jun. 10, 2014 (GB) .................................. 1410323.8

(51) Int. Cl.
| | |
|---|---|
| F02D 19/00 | (2006.01) |
| F02D 19/06 | (2006.01) |
| F02D 41/00 | (2006.01) |
| G01N 25/22 | (2006.01) |
| F02M 43/04 | (2006.01) |
| G01N 33/28 | (2006.01) |
| F02D 41/14 | (2006.01) |

(52) U.S. Cl.
CPC ..... *F02D 19/0626* (2013.01); *F02D 19/0642* (2013.01); *F02D 41/0025* (2013.01); *F02D 41/0027* (2013.01); *F02D 41/1446* (2013.01); *F02M 43/04* (2013.01); *G01N 25/22* (2013.01); *G01N 33/2829* (2013.01); *F02D 19/0689* (2013.01); *F02D 2041/1433* (2013.01); *F02D 2200/0414* (2013.01); *F02D 2200/0612* (2013.01); *Y02T 10/36* (2013.01)

(58) Field of Classification Search
CPC . F02D 19/0642; F02D 19/0626; F02M 43/04; G01N 25/22
See application file for complete search history.

(56) References Cited

U.S. PATENT DOCUMENTS

| | | |
|---|---|---|
| 7,392,129 B2 | 6/2008 | Hill et al. |
| 7,542,842 B2 | 6/2009 | Hill et al. |

(Continued)

*Primary Examiner* — Kevin A Lathers
(74) *Attorney, Agent, or Firm* — Faegre Baker Daniels LLP (57) ABSTRACT

The system comprises a fuel description module structured to provide a first signal, and a control circuit operable to receive the first signal. The fuel description module comprises a fuel consumption detection package. The fuel consumption detection package an intake manifold temperature sensor and an exhaust temperature sensor, wherein the first signal corresponds to a difference between the exhaust manifold temperature (EMT) and the intake manifold temperature (IMT). The control circuit is responsive to the first signal to produce a second signal indicating a total energy content ($E_{fuel}$) of fuel supplied to the dual-fuel engine. The $E_{fuel}$ value indicating the total energy content provided to the engine from a first fuel and a second fuel.

20 Claims, 4 Drawing Sheets

(56) References Cited

U.S. PATENT DOCUMENTS

2009/0223467 A1\* 9/2009 McKnight ................ F23D 1/00
123/23
2013/0179050 A1 7/2013 Munshi et al.

\* cited by examiner

EXHAUST PARAMETER BASED DUAL FUEL ENGINE POWER VIRTUAL SENSOR

PRIORITY

The present application is a US non-provisional application that claims priority to Great Britain Patent Application GB1410323.8 titled "EXHAUST PARAMETER BASED DUAL FUEL ENGINE POWER VIRTUAL SENSOR" filed Jun. 10, 2014. The disclosure of which is hereby expressly incorporated by reference.

FIELD OF THE DISCLOSURE

The present disclosure relates generally to systems for controlling dual-fuel internal combustion engines, and more specifically to systems for determining fuel content being supplied to a dual-fuel internal combustion engine.

BACKGROUND

Dual-fuel engines, such as those operating using diesel fuel and natural gas (or other pilot ignited gaseous fuel), are utilized in vehicles, in pumping applications, as well as other applications. Diesel fuel has a relatively constant and known composition that has a known and predictable energy content per unit of mass thereof. Natural gas, however, is comprised of multiple elements such as Methane, Ethane, Propane, Hexane, Pentane, Butane, and others. Not all of the constituent gasses are combustible. Even those components that are combustible have differing amounts of energy per unit mass thereof. Still further, when obtaining gas, it is unknown how much of the mass and/or volume thereof is combustible fuel. Accordingly, when obtaining natural gas, the amount of energy present in a unit mass is not immediately known.

Engines are produced having a load capacity (capacity for torque, power, or combinations thereof). Exceeding this load capacity subjects the engine and its constituent parts to premature failing and overall reduction in the expected life thereof. Fueling decisions (and other decisions) related to the engine are made with an attempt to keep the engine operating within its rated capacity.

When an engine is operating near capacity, an increase in energy provided to the engine (such as via a particularly fuel with high energy content per unit mass and/or volume) has the potential to cause the engine to operate above its rated capacity.

One solution to keep an engine operating below its capacity is to set the engine rating at an artificially low level such that any energy variability from the fuel is unable and/or very unlikely to send the engine above its design capacity. However, this prevents the engine from being fully utilized under normal fueling conditions.

What is therefore needed is a system for monitoring engine operation and determining the energy present in the fuel to allow the engine to take such energy determinations into account.

DETAILED DESCRIPTION

For the purposes of promoting an understanding of the principles of the invention, reference will now be made to a number of embodiments illustrated in the drawings and specific language will be used to describe the same. It will nevertheless be understood that no limitation of the scope of the invention is thereby intended.

Briefly, in one example, a system for determining energy content of fuel supplied to a dual-fuel engine is provided. The system comprises a fuel description module structured to provide a first signal, and a control circuit operable to receive the first signal. The fuel description module comprises a fuel consumption detection package. The fuel consumption detection package is an intake manifold temperature sensor and an exhaust temperature sensor, wherein the first signal corresponds to a difference between the exhaust manifold temperature (EMT) and the intake manifold temperature (IMT). The control circuit is responsive to the first signal to produce a second signal indicating a total energy content ($E_{fuel}$) of fuel supplied to the dual-fuel engine. The $E_{fuel}$ value indicating the total energy content provided to the engine from a first fuel and a second fuel.

In another example, a method of determining energy in fuel supplied to a dual-fuel engine is provided comprising determining at least one of a temperature of an exhaust gas of a dual-fuel internal combustion engine (EMT) and a temperature of a dual-fuel engine intake charge (IMT); and producing, by an engine control unit, a first signal indicating a total energy content ($E_{fuel}$) of fuel supplied to the dual-fuel engine, the signal being at least partially derived from the at least one temperature of an exhaust gas of a dual-fuel internal combustion engine (EMT), a temperature of a dual-fuel engine intake charge (IMT), the $E_{fuel}$ comprising the total energy content from a first fuel and a second fuel provided to the engine.

In yet another example, a system is provided comprising: a dual fuel internal combustion engine comprising a direct injected liquid first fuel and a gaseous second fuel having a combustible fraction therein; an intake manifold temperature sensor and an exhaust temperature sensor, wherein a first signal corresponds to a difference between the exhaust manifold temperature (EMT) and the intake manifold temperature (IMT); a fuel description module structured to provide the first signal corresponding to a difference between the EMT and the IMT; and a control circuit operable to receive the first signal, and responsive to the first signal to produce a second signal indicating an energy content of the combustible fraction of the second fuel.

Figure 1:
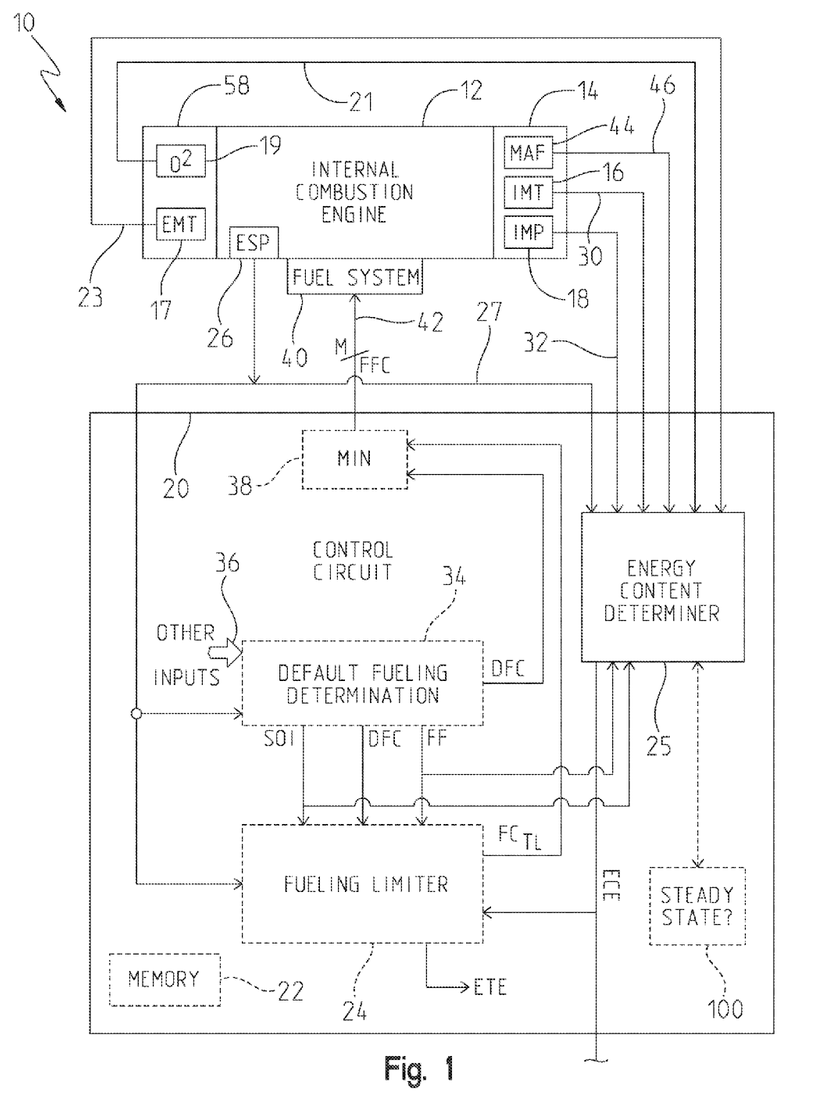
FIG. 1 is a diagrammatic illustration of one embodiment of a system for fueling an engine, in accordance with the present disclosure.

Referring now to FIG. 1, one embodiment of a system 10 for controlling engine 12 is shown. System 10 includes an internal combustion engine 12 having an intake manifold 14 coupled thereto. An intake manifold temperature sensor 16 is disposed within, or otherwise disposed in fluid communication with, manifold 14. Sensor 16 is preferably a temperature sensor of known construction that is operable to sense the temperature within the intake manifold 14 and produce an intake manifold temperature (IMT) signal corresponding thereto. Manifold 14 includes an intake manifold pressure sensor 18 is disposed therewithin, or otherwise disposed in fluid communication therewith, wherein sensor 18 is preferably of known construction and operable to sense a pressure within manifold 14 and produce an intake manifold pressure (IMP) signal corresponding thereto.

Engine 12 includes an exhaust manifold 58 coupled thereto. An exhaust manifold temperature sensor 17 is disposed within, or otherwise disposed in fluid communication with manifold 58. Sensor 17 is illustratively a temperature sensor of known construction that is operable to sense the temperature within the exhaust manifold 58 and produce an exhaust manifold temperature (EMT) signal corresponding thereto. In certain embodiments, an exhaust oxygen sensor 19 is disposed within exhaust manifold 58 or otherwise disposed in fluid communication with exhaust gas within or downstream of the exhaust manifold 58. Sensor 19 is illustratively an oxygen sensor of known construction that is operable to sense oxygen content of the exhaust gas within (or downstream of) the exhaust manifold 58 and produce an exhaust gas oxygen ($O_{EXH}$) signal corresponding thereto. It should be appreciated that while oxygen sensor 19 is described as being optional, in embodiments where oxygen sensor 19 is present, other sensors, such as temperature sensors 16, 17 are optional. Still further, while oxygen sensor 19 is disclosed herein, everywhere that an oxygen sensor is mentioned, it is envisioned that a lamda sensor could also be used. Accordingly, the use of the term oxygen sensor herein is intended to be inclusive of lamda sensors.

Engine 12 includes an engine speed sensor 26 operable to sense rotational speed of the engine 12 and produce an engine speed (ESP) signal corresponding thereto. Sensor 26 is illustratively of known construction, and in one embodiment sensor 26 is a Hall effect sensor operable to sense passage thereby of a number of teeth forming part of a gear or tone wheel. Alternatively, sensor 26 may be a variable reluctance sensor or other known speed sensor, and in any case engine speed sensor 26 is operable to produce an engine speed signal indicative of engine rotational speed. In one embodiment, sensor 26 provides an indication of the revolutions per minute (RPM) of engine 12.

Engine 12 further includes a fuel system 40 responsive to one or more final fuel commands (FFC) to supply fuel to engine 12. Fuel system 40 is preferably an electronically controlled fuel system of known construction, wherein the operation thereof is generally known in the art.

Central to system 10 is a control circuit 20 that is illustratively microprocessor-based and is generally operable to control and manage the overall operation of engine 12. Control circuit 20 includes a memory unit 22 as well as a number of inputs and outputs for interfacing with various sensors and systems coupled to engine 12, such as those just described hereinabove. Control circuit 20, in one embodiment, may be a known control unit sometimes referred to as an electronic or engine control module (ECM), electronic or engine control unit (ECU) or the like, or may alternatively be any control circuit capable of operation as will be described in greater detail hereinafter. In any case, control circuit 20 includes a default fueling determination block 34 receiving the engine speed signal (ESP) from engine speed sensor 26 via signal path 27, as well as a number of additional input signals 36. Block 34 is responsive to the ESP signal on signal path 27 as well as-one or more of the additional signals 36 to compute a default fueling command (DFC) in accordance with techniques well-known in the art. The default fueling command DFC may be an unrestricted fueling command that is used as the final fueling command FFC produced on any number, M, of signal paths 42 for controlling fuel system 40, wherein M may be any positive integer. As it relates to the present disclosure, however, the default fueling determination block 34 may alternatively or additionally include one or more fuel limiting algorithms designed to achieve certain engine operational goals, wherein the default fueling command DFC produced by block 34 represents an unrestricted fueling command that has been limited by one or more such fuel limiting algorithms.

In accordance with the present disclosure, control circuit 20 further includes a fueling limiter block 24 and an energy content determiner block 25. Fueling limiter block 24 receives the engine speed signal (ESP) from engine speed sensor 26 via signal path 27, and a fuel quality content signal ($G_{quality}$ and/or energy content estimate (ECE) from energy content determiner block 25. In the present embodiment, fuel quality content signal is an indication of the energy present in the fuel. Fueling limiter block 24 further receives the default fueling command (DFC) from the default fueling determination block 34.

In a general sense, the default fueling command (DFC) may include additional information such as but not limited to timing information relating to the start-of-injection (SOI) and fuel quantity information relating to mass fuel flow (FF), as these terms are understood to those skilled in the art. In one embodiment, the default fueling determination block 34 is configured to supply the fueling limiter block 24 with the default fueling command (DFC), and block 24 is operable to determine from DFC the values of SOI and FF in a manner known in the art. Alternatively, the default fueling determination block 34 may be configured to supply the fueling limiter block 24 with the SOI and/or FF values directly, wherein block 24 is operable to process either one, or both, of these values in a manner to be more fully described hereinafter.

Figure 3:
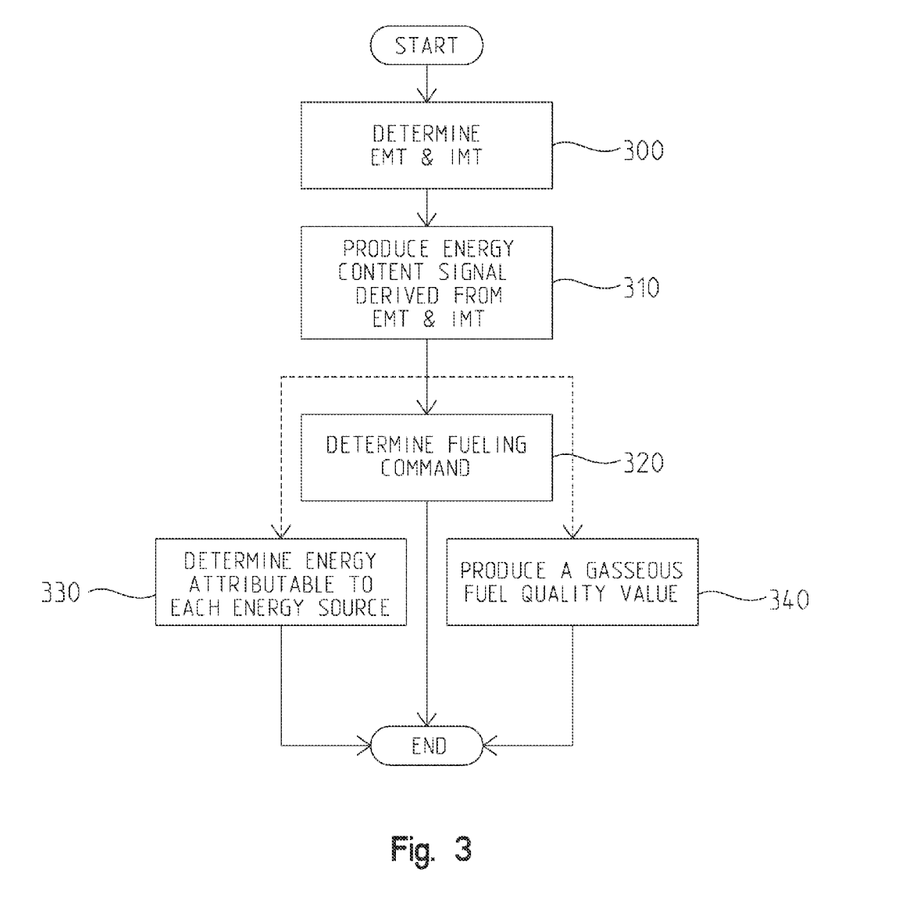
FIG. 3 is a flowchart illustrating one embodiment of software instructions for determining energy content according to a first embodiment shown in FIG. 2.
Figure 4:
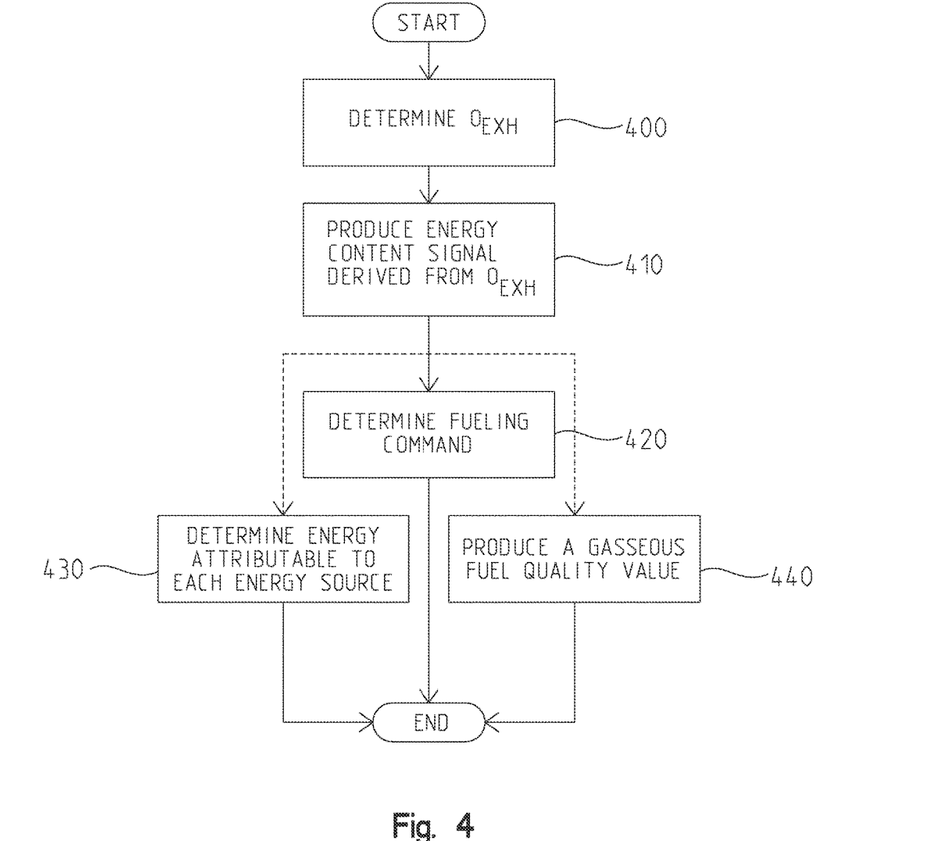
FIG. 4 is a flowchart illustrating one embodiment of software instructions for determining energy content according to an alternative embodiment shown in FIG. 2.

Energy content determiner block 25 receives the intake manifold temperature signal (IMT) from the intake manifold temperature sensor 16 via signal path 30, exhaust manifold temperature signal (EMT) from temperature sensor 17 via path 23 (block 300), the intake manifold pressure signal (IMP) from intake manifold pressure sensor 18 via signal path 32, mass air flow signal (MAF) from mass air flow sensor 44 via path 46, engine speed signal (ESP) from engine speed sensor 26 via path 27, and (potentially alternatively) oxygen content signal ($O_{EXH}$) from oxygen sensor 19 via path 21 (block 400). Energy content determiner block 25 also illustratively receives the start-of-injection (SOI) and fuel quantity information relating to mass fuel flow (FF) from default fueling determination block 34.

As described above, intake manifold 14 include a mass air flow sensor (MAF) 44 of known construction supplying a charge flow value to block 25. However, embodiments are envisioned where the mass charge flow value (ECF) is supplied by a known software algorithm operable to compute a charge flow estimate based on certain engine operating parameter values.

In cases where the charge flow value (ECF) is estimated in accordance with a known estimation algorithm, one preferred embodiment of control circuit 20 includes a charge flow determination block (not shown).

Figure 2:
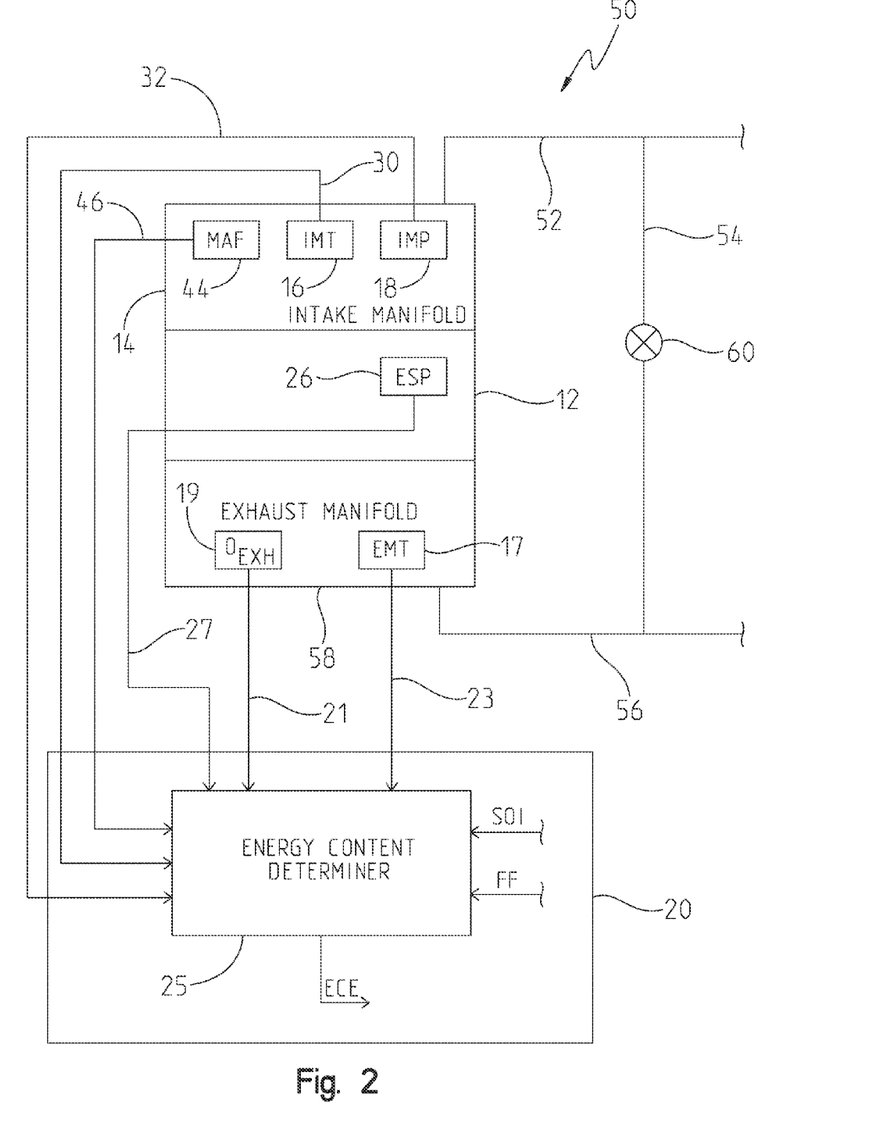
FIG. 2 is a diagrammatic illustration of one embodiment of a system for determining an energy content in fuel by the energy content determiner block of FIG. 1.

Referring to FIG. 2, a first embodiment system is shown for determining an energy content in fuel; e.g., total effective combustion energy applied to a flywheel of engine 12 after thermodynamic losses, total fuel energy available, total fuel energy that goes to exhaust temperature generation, and/or total fuel energy supplied to the engine inlet. In any case, system 50 includes several components in common with system 10 of FIG. 1, and like numbers are therefore used to identify like components.

System 50 includes an internal combustion engine 12 having an intake manifold 14 fluidly coupled to an intake conduit 52, wherein intake manifold 14 receives fresh air via conduit 52. Exhaust manifold 58 of engine 12 expels exhaust gas to ambient via exhaust conduit 56, and an EGR valve 60 is disposed in fluid communications with the intake and exhaust conduits 52 and 56 respectively via conduit 54. An engine speed sensor 26 is electrically connected to block 25 via signal path 27. An intake manifold temperature sensor (IMT) 16 is disposed in fluid communication with the intake manifold 14 of engine 12, and is electrically connected to the energy content determiner block 25 of control circuit 20 via signal path 30. Intake manifold 14 also includes an intake manifold pressure sensor (IMP) 18 in fluid communication therewith and electrically connected to the energy content determiner block 25 of control circuit 20 via signal path 32. Exhaust manifold 58 includes exhaust manifold temperature sensor (EMT) 17 in fluid communication therewith. Exhaust manifold temperature sensor 17 is electrically connected to energy content determiner block 25 of control circuit 20 via signal path 23.

In one embodiment, the energy content determiner block 25 of the control circuit 20 is operable to compute an estimate of the energy content in fuel supplied to engine 12. In this embodiment, $\dot{m}_{fuel}$ is used as an indication of energy and is computed by using the formula:

$$\dot{m}_{fuel} = \frac{C_{P_{air}}}{X_f \times LHV_{fuel}} \times \dot{m}_{chrg} \times (EMT - IMT)$$

Or $$E_{Fuel} = \frac{C_{P_{air}}}{X_f} \times \dot{m}_{chrg} \times (EMT - IMT)$$

where $C_{P_{air}}$ the specific heat of air, $X_f$ is the fraction of burned fuel that goes into heating exhaust gases rather than as work to the crankshaft or heat lost to the engine coolant and block, $LHV_{fuel}$ is the lower heating value of the fuel which represents an amount of energy released during the combustion of the fuel (or energy content per mass of a fuel), $\dot{m}_{chrg}$ is the charge mass flow, EMT is exhaust manifold temperature, IMT is intake manifold temperature, $\dot{m}_{fuel}$ is the mass of the fuel, and $E_{Fuel}$ is the total energy of the fuel. In one embodiment, the terms $C_{P_{air}}$ and $X_f$ are able to be combined into/replaced by a term $C_{fuel}$ such that the above formula can be re-written as:

$$E_{fuel} = C_{fuel} \times \dot{m}_{chrg} \times (EMT - IMT)$$

$C_{fuel}$ is able to be estimated by the formula:

$$C_{fuel} = C_1 + C_2 \times ESP + C_3 \times IMP + C_4 \times SOI$$

Each of $C_{1-4}$ is a coefficient, ESP is the engine speed (such as RPM), IMP is the intake manifold pressure, and SOI is the start of injection. Additional embodiments estimate $C_{fuel}$ using less than all of these components. In practice, $C_{fuel}$ nearly approximates a constant. Accordingly, embodiments are envisioned that use only $C_1$ as $C_{fuel}$. However, the addition of the other components and their coefficients increase the precision of the estimation. In one embodiment, the ratio of diesel fueling to charge flow is included to provide an indication of a substitution ratio. This term accounts for changes in combustion efficiency. Accordingly, embodiments are envisioned where $C_{fuel}$ is estimated according to any of the following additional formulas:

$$C_{fuel} = C_1$$

$$C_{fuel} = C_1 + C_2 \times ESP$$

$$C_{fuel} = C_1 + C_2 \times ESP + C_3 \times IMP$$

$$C_{fuel} = C_1 + C_2 \times ESP + C_3 \times IMP + C_4 \times SOI + C_5 \times \text{Diesel Fueling/Charge Flow}$$

$$C_{fuel} = C_1 + C_2 \times ESP + C_3 \times IMP + C_4 \times SOI + C_5 \times \text{Rail Pressure}$$

According to a second embodiment, the energy content determiner block 25 of the control circuit 20 is operable to compute an estimate of the energy content in fuel supplied to engine 12 by monitoring the oxygen consumed by the combustion process. The components of the second embodiment are also shown in FIG. 2. It should be appreciated that certain features shown in FIG. 2 need not be present depending on which embodiment of energy content determiner block 25 is being employed. Natural gas and diesel have similar profiles with respect to energy content per amount of oxygen consumed. Accordingly, when looking to oxygen content as a representation of energy within (or released from) fuel, any variation in the fuel composition (variation within natural gas, or variation in substitution ratio) can largely be ignored. With respect to oxygen consumption, while most oxygen is consumed to facilitate combustion of hydrocarbons, combustion is not 100% efficient. As an example, some oxygen is consumed in the creation of carbon monoxide. In some embodiments, an estimate of combustion efficiency may improve fuel energy determination based on exhaust oxygen measurement. FIG. 2 shows energy content determiner block 25 obtaining an oxygen content signal ($O_{EXH}$) from oxygen sensor 19 via path 21.

In this embodiment, energy content is estimated by using the formula:

$$E_{Fuel} = FAF \times (O_{Amb}/\lambda) \times LHV_{PerO}$$

where FAF is fresh air flow[kg/sec], $O_{Amb}$ is the Oxygen mass fraction in air, $\lambda$ is a function of a reading from the exhaust oxygen sensor (or lambda sensor), and $LHV_{PerO}$ is the LHV per unit O2 [kJ/kg]. FAF is the dry air part of the mass air flow. The influence from humidity can be removed by measuring ambient temperature, pressure and relative humidity or partly compensated by an estimate of them. As previously noted, the resulting value ($E_{Fuel}$) may be further altered by a combustion efficiency value to determine the actual energy present in the provided fuel, if desired. This $E_{Fuel}$ value can then be output as an energy content estimate (ECE) or it can be further modified (such as by dividing by the LHV of the fuel (actual or estimated) to produce a mass flow value).

In one embodiment, control circuit 20 further includes a steady-state determination block 100. Steady state determination block 100 illustratively receives the same inputs or a subset of the inputs that are received by energy content determiner block 25. Steady state determination block 100 determines when one or more of the inputs to energy content determiner block 25 are considered to be in a steady state (varying by less than a threshold amount for above a threshold amount of time). Upon satisfying the conditions to be considered steady state, steady-state determination block 100 sends a steady state signal to energy content determiner block 25 that indicates that the system can be considered to be at a steady state. Upon receiving such steady state signal and in response thereto, energy content determiner block 25 uses the input signals (such as those on paths 21, 23, 30, 32, 46, 27, or otherwise) to calculate/estimate the energy value(s) as described above.

In addition to the above embodiments, embodiments are envisioned where other parameters are used to further refine the estimation of fuel energy flow. Such additional parameters include, but are not limited to, exhaust manifold pressure and turbo speed.

As noted, in a dual fuel engine, the fuel mass flow is comprised of multiple fuels (such as diesel fuel and natural gas). Energy content determiner block 25 is further operable to determine/estimate the constituent portions of each fuel (energy source) that is supplied (energy from diesel, energy from natural gas) (block 330, 430).

Given the above formulas, energy content determiner block 25 determines/estimates the energy content of the fuel, and/or energy flux across the engine (blocks 310, 410). While the energy content model is preferably provided in the form of an equation stored within block 25 or memory unit 22, the present disclosure contemplates that the model may alternatively be provided in the form of one or more graphical representations, tables, and/or the like. In any case, the energy content determiner block 25 is preferably operable to compute a model-based energy content estimate (ECE) for use in accordance with other aspects of the present invention, and/or for use by other algorithms and/or control strategies within control circuit 20.

In one embodiment this value is provided to an output port such that external devices are able to receive this value for informational or use purposes. In the embodiment of FIG. 1, this value is provided to fueling limiter block 24.

It should be appreciated that the calculated/estimated values for energy received/consumed by engine 12 represent energy that is a combination of energy from both fuels in the dual fuel system (illustratively diesel and natural gas) ($E_{total} = E_{fuel1} + E_{fuel2}$). For each fuel, the energy supplied thereby is the mass flow of that fuel multiplied by its LHV ($E_{fuel1} = \dot{m}_{fuel1} * LHV_{fuel1}$). As part of fueling engine 12, default fueling determination block 34 and/or fueling limiter block 24 issue commands to control the fueling. These commands illustratively include commands for one or more of the dual fuels (such as mass flow commands). Accordingly, from the command values and other known information regarding the LHV of one or more of the fuels, further estimations can be calculated to determine the energy being provided by each of the constituent fuels. Still further, other values describing a quality of one of the fuels can be determined. These values can then be output to other logic blocks, to an external port of control circuit 20, or otherwise. In one embodiment, where the dual fuels are diesel and natural gas, the desired fueling amount of diesel ($m_{liquid}$) and natural gas are determined from default fueling determination block 34 and/or fueling limiter block 24. Diesel is known to have a consistent LHV. Accordingly, given the calculated overall energy, energy content determiner block 25 is able to determine the energy attributable to one fuel (diesel) and then determine that the balance of the determined $E_{Fuel}$ is attributable to the second fuel (natural gas). Still further, the system is operable to measure and/or estimate an amount of the second fuel that was used to generate $E_{Fuel}$. Given the energy attributable to the second fuel, and the amount of second fuel, an effective LHV of the natural gas being consumed ($G_{quality}$) (block 340, 440) can be calculated/determined/estimated. This value is then available to be output within or externally of control circuit 20.

Still further, in one embodiment, knowing the combustible mass of the natural gas allows a calculation/determination/estimation of what fraction of the fuel is represented by that combustible mass. The mass of the combustible natural gas is compared to total gaseous flow to obtain the combustible gas fraction.

Referring again to FIG. 1, the fueling limiter block 24 illustratively includes a model for estimating/calculating the torque produced by the engine for a given set of operating parameters. This model is present as a torque curve, a formula, table, or otherwise. Fueling limiter block 24 also includes information regarding the load ratings and/or torque production ratings for engine 12. Fueling limiter block takes the input ECE value and uses that to calculate the torque produced by the engine via an engine torque estimation model. When the torque produced by the engine approaches or exceeds the rated limits of the engine, exceeds a threshold value near the rated limits, or otherwise is determined to be operating under a high load (for example operating at greater than 50% of its rated load value), fueling limiter block 24 generates a torque-limited fueling command ($FC_{TL}$) as a function of the engine torque estimation model (block 320, 420). The torque-limited fueling command ($FC_{TL}$) is a fueling command that keeps engine 12 within its ratings for the given fuel having the calculated energy therein. The torque-limited fueling command $FC_{TL}$ is illustratively a function of the default fueling command (DFC) that is limited by block 24 as a function of an imposed maximum torque limit ($T_{EL}$) according to the torque estimation model of the present disclosure. In any case, the default fueling command (DFC) produced by the default fueling determination block 34 and the torque-limited fueling command $FC_{TL}$ produced by the fueling limiter block 24 are both provided to a MIN block 38 operable to produce as the final fueling command FFC on signal path 42 a minimum value thereof. In such a manner, control circuit 20 operates to enforce the torque curve of engine 12 and to keep engine 12 within its rated limits. Control circuit 20 thereby issues a signal controlling the ratio of the amount of the first fuel to the amount of the second fuel that is provided to the dual fuel engine It should be appreciated that the various sensors (16, 17, 18, 19, 44, 26, etc.) are fairly characterized as being or as part of fuel consumption detection packages that are part of fuel description modules insomuch as they are measuring a property of engine 12 that is directly or indirectly describing a property of the fuel.

The above detailed description and the examples described therein have been presented for the purposes of illustration and description only and not for limitation. For example, the operations described may be done in any suitable manner. The method steps may be done in any suitable order still providing the described operation and results. It is therefore contemplated that the present embodiments cover any and all modifications, variations or equivalents that fall within the spirit and scope of the basic underlying principles disclosed above and claimed herein.

What is claimed is:

1. A system for determining energy content of fuel supplied to a dual-fuel engine comprising:
   a fuel description module comprising a fuel consumption detection package including an intake manifold temperature sensor that senses an intake manifold temperature (IMT) within an intake manifold and an exhaust manifold temperature sensor that senses an exhaust manifold temperature (EMT) within an exhaust manifold, and a control circuit comprising an energy content determiner, wherein
the fuel description module provides the IMT and EMT to the energy content determiner,
the energy content determiner provides a first signal that corresponds to a difference between the EMT and the IMT, and
the control circuit, in response to the first signal, calculates an estimated total energy content ($E_{fuel}$) of fuel supplied to the dual-fuel engine and produces a second signal indicating the calculated $E_{fuel}$ of fuel supplied to the dual-fuel engine, the $E_{fuel}$ comprising the total energy content estimated from a first fuel and a second fuel provided to the engine.

2. The system of claim 1, wherein the control circuit is responsive to the first signal to control a fuel system that controls at least one of the first fuel and the second fuel being supplied to the engine.

3. The system of claim 1, wherein the control circuit is further operable to determine or estimate at least one of a total mass flow rate of the first fuel and the second fuel, an amount of the total fuel that heats the exhaust gases on combustion ($X_f$), and a lower heating value of the combined first fuel and the second fuel (LHV).

4. The system of claim 1, wherein the control circuit is further operable to determine a charge flow value and to determine a value that expresses energy as function of intake gas heat capacity, wherein the control circuit estimates energy present in fuel supplied to the engine according to the formula:

$$E_{fuel} = (C_{Pair}/X_f) \times m_{charge} \times (EMT - IMT),$$

wherein the $E_{fuel}$ is the total energy of the first fuel and the second fuel, wherein $C_{Pair}$ is the heat capacity of the charge flow, wherein $X_f$ is an amount of the total fuel that heats the exhaust gases on combustion, and wherein the $m_{charge}$ is the mass flow rate of the charge flow.

5. The system of claim 4, wherein the first fuel comprises a liquid fuel and wherein the second fuel comprises a gaseous fuel, and wherein the control circuit is further responsive to the second signal to produce a third signal ($G_{quality}$) indicating a gas quality value.

6. The system of claim 5, wherein the control circuit is further responsive to produce the $G_{quality}$ by subtracting an energy amount attributable to the first fuel from the $E_{fuel}$ to determine an energy amount attributable to the second fuel.

7. The system of claim 6, further including obtaining one of a measurement and estimation of an amount of the second fuel consumed to produce $E_{fuel}$ such that an estimation of the effective LHV of the second fuel is obtained.

8. The system of claim 4, wherein said control circuit is further operable to determine at least one of start of injection (SOI), engine speed (ESP/RPM), intake manifold pressure (IMP), and rail pressure (RP) values corresponding to a fueling command.

9. The system of claim 8, where said control circuit is operable to estimate an empirical heat gain coefficient ($C_{fuel}$) according to an equation selected from the group of:

$$C_{fuel} = C_1 + C_2 \times RPM + C_3 \times IMP, \quad 1)$$

and $$C_{fuel} = C_1 + C_2 \times RPM + C_3 \times IMP + C_4 \times SOI, \quad 2)$$

wherein the control circuit is further responsive to produce the $E_{fuel}$ responsive to the $C_{fuel}$.

10. The system of claim 1, wherein the control circuit is further operable to determine a charge flow value and to determine a value that expresses energy as function of intake gas heat capacity, wherein the control circuit estimates energy present in fuel supplied to the engine according to the formula $E_{fuel} = (C_{fuel}) \times m_{charge} \times (EMT - IMT)$, wherein the $E_{fuel}$ is the total energy of the first fuel and the second fuel, and wherein the $m_{charge}$ the mass is flow rate of the charge flow.

11. The system of claim 1, wherein the control circuit is responsive to said second signal to produce a third signal, the third signal controlling the ratio of the amount of the first fuel to the amount of the second fuel that is provided to the dual fuel engine.

12. A method of determining energy in fuel supplied to a dual-fuel engine comprising:
determining a temperature of an exhaust gas of a dual-fuel internal combustion engine (EMT) with an exhaust manifold temperature sensor and a temperature of a dual-fuel engine intake charge (IMT) with an intake manifold temperature sensor;
estimating, by an engine control unit, a total energy content ($E_{fuel}$) of fuel supplied to the dual-fuel engine;
producing, by the engine control unit, a first signal indicating the estimated $E_{fuel}$ of fuel supplied to the dual-fuel engine, wherein the first signal is at least partially derived from the temperature of the exhaust gas of the dual-fuel internal combustion engine (EMT) and the temperature of the dual-fuel engine intake charge (IMT), and wherein the $E_{fuel}$ of the first signal comprises the total energy content from a first fuel and a second fuel provided to the engine.

13. The method of claim 12, further including determining a fueling command for controlling a fuel system supplying at least one of the first fuel and the second fuel to said engine based upon the indicated energy content within said fuel.

14. The method of claim 12, wherein the first signal is indicative of the energy extracted from both a first and second fuel, the method further including determining portions of the energy attributable to each of the first and second fuels.

15. The method of claim 14, wherein at least one of the first and second fuels is a gaseous fuel, the method further including producing a gaseous fuel quality diagnostic communication responsive to determining the portion of the energy attributable to the gaseous fuel.

16. The method of claim 12, further including producing a gaseous substitution ratio signal responsive to the produced first signal.

17. The method of claim 12, wherein the at least one of the temperature of the exhaust gas of the dual-fuel internal combustion engine (EMT) and the temperature of the dual-fuel engine intake charge (IMT) is determined at a time when such value is exhibiting a steady state value.

18. A system, comprising:
a dual fuel internal combustion engine comprising a direct injected liquid first fuel and a gaseous second fuel therein;
an intake manifold temperature sensor that senses an intake manifold temperature (IMT) within an intake manifold and an exhaust manifold temperature sensor that senses an exhaust manifold temperature (EMT) within an exhaust manifold;
a fuel description module structured to provide the EMT and the IMT to an energy content determiner; and a control circuit comprising the energy content determiner, wherein
the energy content determiner provides a first signal that corresponds to a difference between the EMT and the IMT,
the control circuit, in response to the first signal, calculates an estimated effective energy content of the second fuel and to produce a second signal indicating the estimated effective energy content of the second fuel.

19. The system of claim 18, wherein said control circuit is further operable to determine at least one of start of injection (SOI), engine speed (RPM), intake manifold pressure (IMP), and rail pressure (RP) values corresponding to a fueling command, wherein said control circuit is operable to estimate an empirical heat gain coefficient ($C_{fuel}$) according to an equation selected from:

$$C_{fuel} = C_1 + C_2 \times RPM + C_3 \times IMP, \quad \quad 1)$$

and $$C_{fuel} = C_1 + C_2 \times RPM + C_3 \times IMP + C_4 \times SOI, \quad \quad 2)$$

and wherein the control circuit is further responsive to produce energy content ($E_{fuel}$) in response to the $C_{fuel}$.

20. The system of claim 19, wherein the control circuit is further operable to determine a charge flow value and to determine a value that expresses energy as function of intake gas heat capacity, wherein the control circuit estimates energy present in fuel supplied to the engine according to the formula $E_{fuel} = (C_{fuel}) \times m_{charge} \times (EMT-IMT)$, wherein the $E_{fuel}$ is the total energy of the first fuel and the second fuel, wherein the $m_{charge}$ is the mass flow rate of the charge flow.

* * * * *